United States Patent [19]

Kambara

[11] Patent Number: 5,366,608

[45] Date of Patent: * Nov. 22, 1994

[54] ELECTROPHORESIS GEL MIGRATION APPARATUS

[75] Inventor: Hideki Kambara, Hachiouji, Japan

[73] Assignee: Hitachi, Ltd., Tokyo, Japan

[*] Notice: The portion of the term of this patent subsequent to Jan. 11, 2011 has been disclaimed.

[21] Appl. No.: 133,851

[22] Filed: Oct. 12, 1993

Related U.S. Application Data

[63] Continuation of Ser. No. 942,605, Sep. 10, 1992, Pat. No. 5,277,780.

[30] Foreign Application Priority Data

Sep. 13, 1991 [JP] Japan .................................. 3-234427

[51] Int. Cl.$^5$ ................................................ C25B 9/00
[52] U.S. Cl. ............................................... 204/299 R
[58] Field of Search ................................... 204/299 R

[56] References Cited

U.S. PATENT DOCUMENTS 4,305,799 12/1981 Schwarz et al. ................ 204/180 G
4,971,677 11/1990 Kambara et al. ................ 204/299 R Primary Examiner—John Niebling
Assistant Examiner—Cybille Delacroix-Muirheid
Attorney, Agent, or Firm—Antonelli, Terry, Stout & Kraus

[57] ABSTRACT

A gel capillary electrophoresis apparatus has gel capillaries (2) filled with gel (2a) that are fixed at both ends thereof on an upper plate 5 and a lower plate (6). The gel capillaries (2) are arranged coarse on the upper plate (5) for sample injection and dense on the lower plate (6) for fluorescence detection. The apparatus is made easy in the sample injection and high in the fluorescence detection efficiency so that throughput of analysis of DNA and the like can be increased, and is available for three-dimensional electrophoresis.

5 Claims, 5 Drawing Sheets

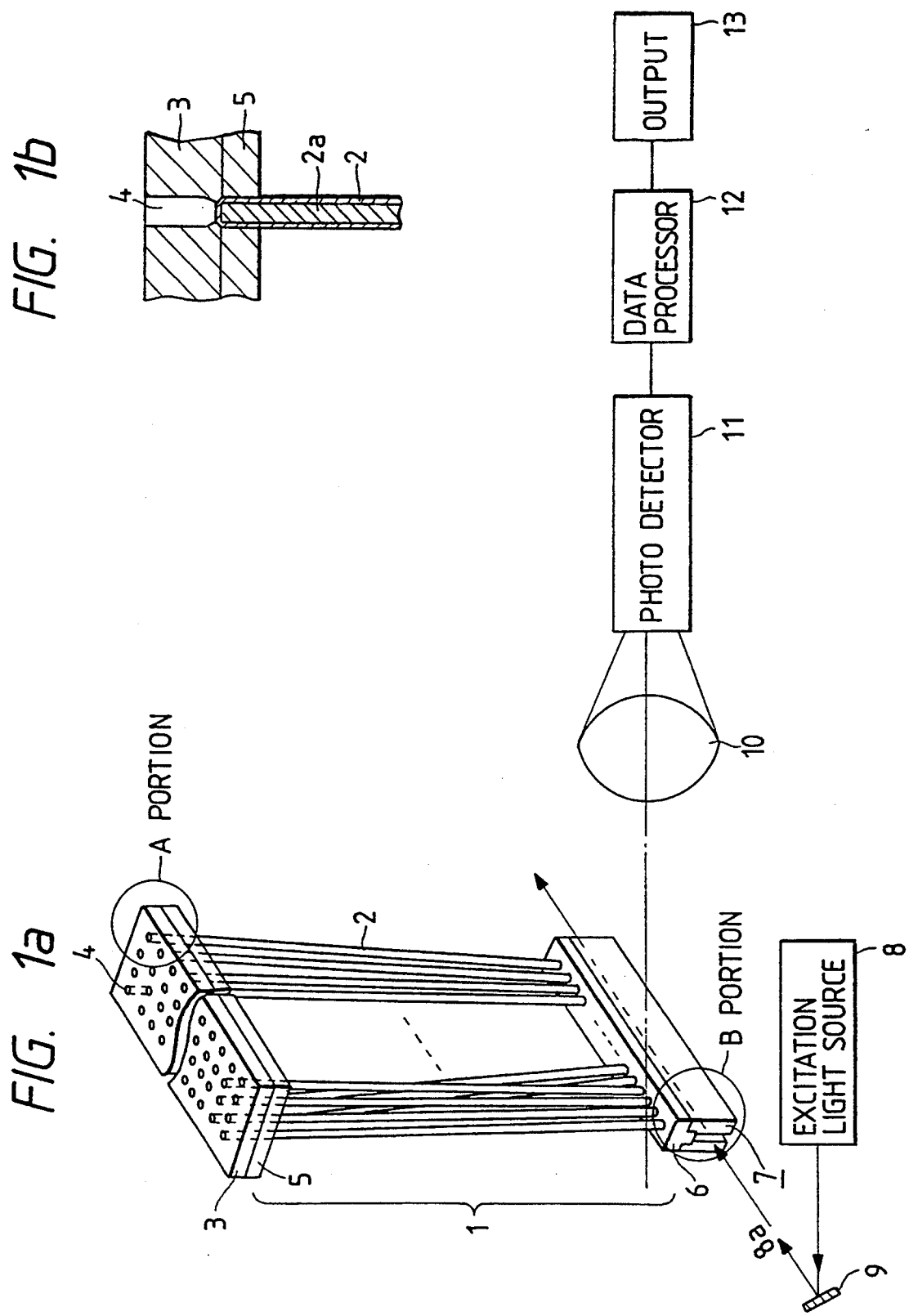

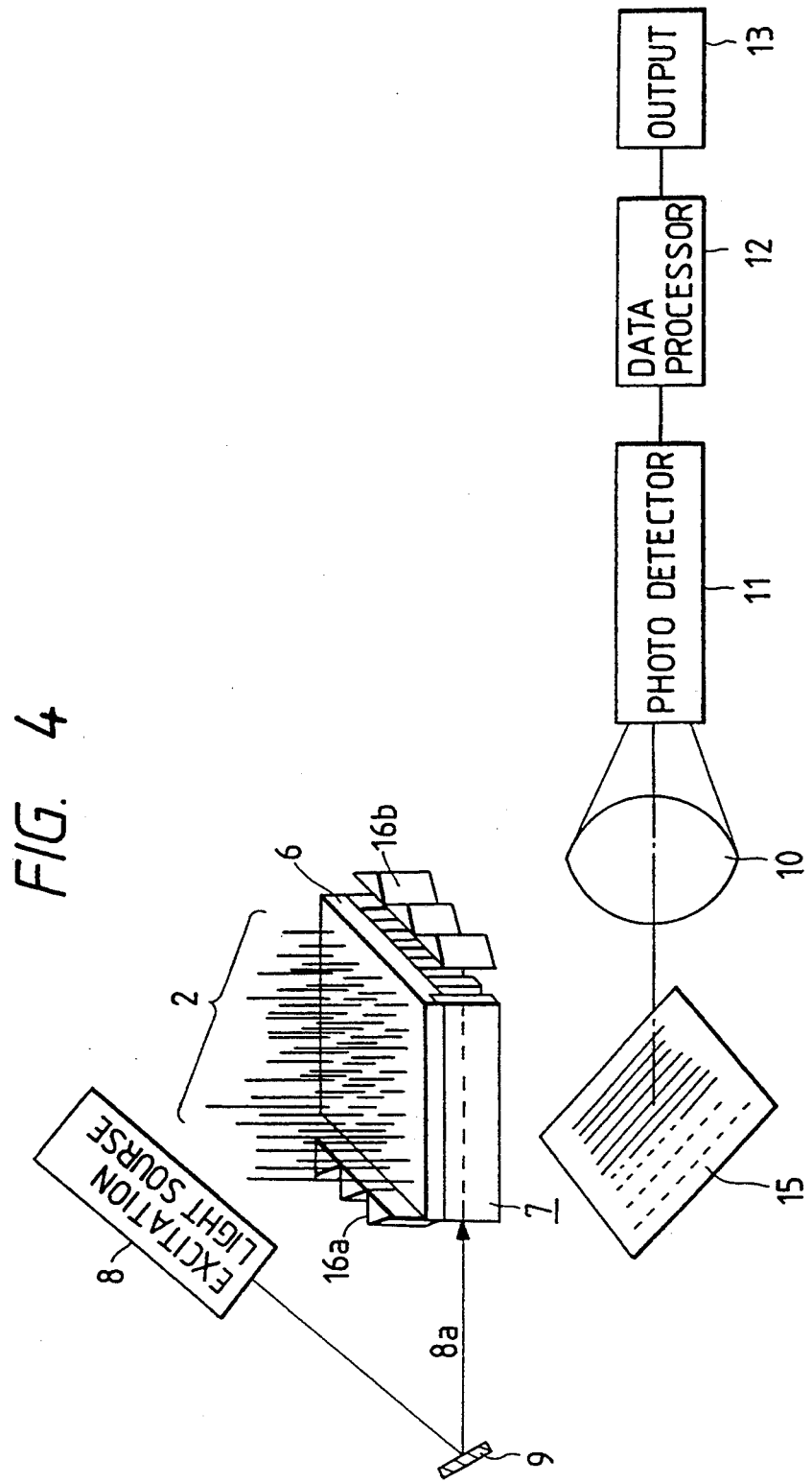

ELECTROPHORESIS GEL MIGRATION APPARATUS

This application is a continuation-in-part of application Ser. No. 07/942,605, filed Sep. 10, 1992 now U.S. Pat. No. 5,277,780.

BACKGROUND OF THE INVENTION

The present invention relates to an electrophoresis gel migration apparatus for electrophoresis separation of a DNA or protein.

Conventionally, base sequence of a DNA has been determined in the way that the DNA was labeled by a radio isotope element and subjected to the electrophoresis gel separation before the separation pattern was transferred onto a film. However, the prior art technique mentioned above has the disadvantage that it is not only troublesome to use the radioactive label, but also it needs too much labor and time. To overcome such problems, a new real-time fluorescent label method has been recently used, as disclosed in the Japanese Patent Application Laid-Open 61-62843.

The fluorescent label method mentioned above uses slab gel, while a further new gel capillary electrophoresis method is now attracting attention. The gel capillary electrophoresis method provides a high-speed, high-sensitive analysis with use of a capillary filled with gel (hereinafter referred to as the gel capillary), as disclosed in the Analytical Chemistry, vol. 62, pp. 900–903, 1990.

The gel capillary electrophoresis is ordinarily made in the way that one capillary tube and a detection lens are built in a package to integrate. The capillary tube can be used repeatedly. However, it is usually discarded whenever it is used a few times as the gel is distorted during the operation. To make possible analysis of many samples at a time, there has been a disclosure that a multiple of gel capillaries are arranged for measurement. In the measurement, the multiple of gel capillaries are retained by the respective holders as disclosed in the BioTechniques, vol. 9, p. 74, 1990.

Any of those measurements having the capillary gel is made in the way that light is irradiated around the end of the capillaries to excite the fluorescent-labeled DNA passing there to emit fluorescence for detection of sample fragments. To make measurement at a high sensitivity and accuracy, the capillaries have to be set precisely.

In order to measure many DNA samples at a time to increase throughput, numbers of gel capillaries have to be arranged. The gel capillaries have to be replaced after a few times of measurement. This means that it must be easy to attach or detach the numbers of gel capillaries and to align their positions. The injection of sample into the gel capillaries has been made with the use of electric field into the ends of the gel capillaries put in sample wells. However, no reports have been made for good workmanship of injecting the sample if the numbers of gel capillaries should be arranged. This is one of the problems to be solved.

Distances of the gel capillaries should be longer with respect to easiness of the sample injection. But, they should be shorter for efficient measurement or the sample fragments. It therefore has been needed to develop an apparatus meeting the both requirements.

SUMMARY OF THE INVENTION

In view of the foregoing, it is an object of the present invention to provide a gel capillary electrophoresis separation portion integrated in such a way that numbers of gel capillaries are coupled at both ends thereof with sample well side and a detection end for detection of sample fragments, in order to make easy attachment or detachment and alignment of the gel capillaries. It is the other object of the present invention to provide a highly sensitive gel capillary electrophoresis apparatus providing good workmanship of sample injection.

Briefly, the foregoing objects are accomplished in accordance with aspects of the present invention by a gel capillary electrophoresis apparatus. The apparatus is of gel capillary cartridge type that, as shown in FIGS. 1a and 1b, can separate the gel capillary electrophoresis separation portion from a sample injection plate 3 having sample wells 4 to be injected with samples and a detector portion 7 for detecting fluorescent light from sample fragments. The apparatus includes a gel capillary cartridge 1 having, in combination, an upper plate 5 of wide area, the gel capillaries 2, and a lower plate 6 of narrow area. The upper plate 5 couples the gel capillaries 2 with the sample injection plate 3 at capillary terminuses thereof from which the samples are injected. The lower plate 6 couples the gel capillaries 2 with the detector portion 7 at detection ends at which the samples migrated are detected. The gel capillary cartridge 1 can be replaced with every measurement. This does not only increase throughput, but also makes the sample injection easy for simple setting of the gel capillaries 2. The gel capillaries 2 are made dense on the narrow area of the detector portion 7 so that any of the lights emitted from the sample fragments can be focused on an high-sensitivity image sensor on the detector portion 7 without shrinking any of remaining image. The detector portion 7 thus provides a highly efficient photodetection.

The gel capillary cartridge 1 can practically hold 20 to 500 gel capillaries 2 so that the throughput of the sample measurement can be increased. The sample injection can be made easy in the way that the gel capillaries 2 are made coarse at the ends arranged and fixed on the upper plate 5 of the gel capillary cartridge 1 and the ends are aligned with a sample holder or injection jig. The gel capillary electrophoresis can be made high in sensitivity as the detector portion 7 can be increased in the detection efficiency in the way that the gel capillaries 2 are made dense at the other ends fixed on the lower plate 6.

The capillaries available for the gel capillaries 2 are not limited in their inside diameter, wall thickness, and length. The inside diameter should be smaller than 0.3 mm, ordinarily 0.1 to 0.2 mm, for convenience of bending. The wall thickness should be usually made 0.1 to 0.2 mm. The length should be practically 10 to 100 cm, ordinarily 30 to 50 cm. Outside diameter of the capillaries should be ordinarily made 0.3 to 0.4 mm.

The detector portion 7 has a gap between bulkheads 7a and 7b provided in parallel, the gap width being virtually equal to the inside diameter of the capillaries. The gap is filled with buffer solution or gel. The buffer solution or gel is irradiated by an excitation light. The excitation light has to be made to irradiate all the migration paths at the same time. If the excitation light is not scanned, it cannot directly irradiate all the capillary tubes at a time. For the reason, the excitation light should irradiate positions at which the samples elute from the capillaries. If the irradiation positions are too close to the lower ends of the capillaries, scattering at the ends of the capillaries affect the measurement. If they are too far from the lower ends, on the other hand, the samples eluted may mix with one another. Both cases are undesirable. In the present invention, it is effective that the excitation light should irradiate positions 0.5 to 1 mm away from the lower ends of the capillaries. If the excitation light, such as laser beam, is scanned for measurement, it may irradiate the capillary tubes themselves because diverged light beams having passed through the capillary tubes are not re-used. It is good that distance between the bulkheads should be virtually equal to the inside diameter of the capillaries of 0.1 to 0.2 mm.

The upper ends of the gel capillaries 2 can be coarse that is spaced not to disturb injection of the samples, say, intervals of 2 to 10 mm. The lower ends should be as dense as possible to increase the fluorescence detection efficiency, say 0.3 to 1 mm. The densities however are limited to those.

BRIEF DESCRIPTION OF THE DRAWINGS

The present invention may be more fully described by reference to the accompanying drawings in which:

FIG. 1a is a schematic view of major parts of an electrophoresis gel migration apparatus of an embodiment of the present invention;

FIG. 1b is a cross-section of a portion (a plane passing a center of any of gel capillaries on a sample injection plate) around a sample injection portion of the electrophoresis gel migration apparatus of the embodiment;

FIG. 4 is a schematic view for major parts of an electrophoresis gel migration apparatus of another embodiment of the present invention in which lower ends of the gel capillaries are arranged in two dimensions on the detector portion; and, FIG. 5 is a cross-section of a portion around a fluorescence detector portion of another embodiment.

DESCRIPTION OF THE PREFERRED EMBODIMENTS

Embodiment 1

The following describes an embodiment 1 of the electrophoresis gel migration apparatus according to the present invention by referring to FIGS. 1a, 1b, 2a, 2b, 2c, 3a, and 3b. FIG. 1a is a perspective view illustrating major parts of a gel capillary electrophoresis migration apparatus in the embodiment 1.

Figure 2A:
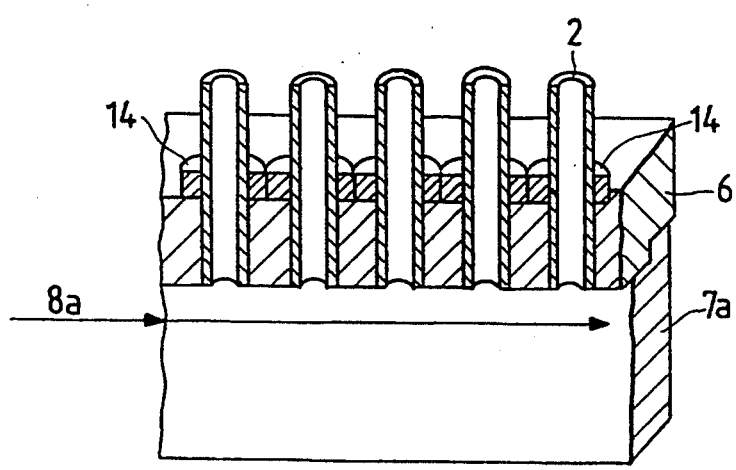
FIGS. 2a, 2b, and 2c are cross-sections on a plane and its variations passing the center of any of the gel capillaries around a fluorescence detector portion of the embodiment.
Figure 3A:
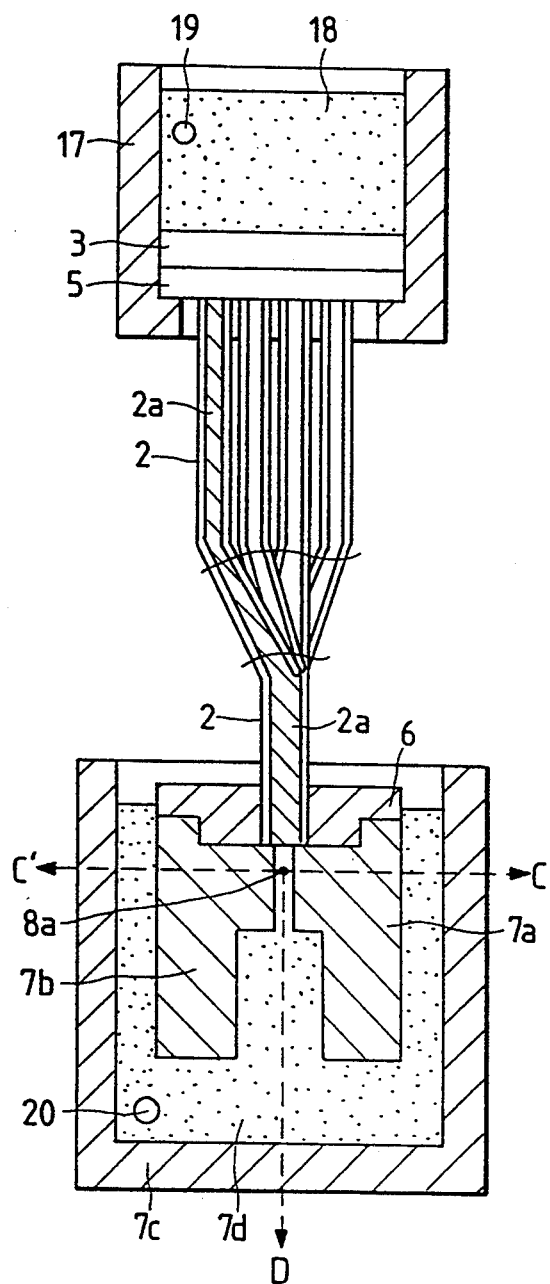
FIG. 3a is a cross-section of the electrophoresis gel migration apparatus of the embodiment of the present invention.

There is provided a gel capillary cartridge 1 in the apparatus. An upper plate 5 of the gel capillary cartridge 1 is coupled with a sample injection plate 3. Sample wells 4 on the sample injection plate 3 are immersed in an upper buffer solution 18 in an upper buffer vessel 17 shown in FIG. 3a. A lower plate 6 of the gel capillary cartridge 1 is coupled with a detector portion 7 that can detect light emitted by sample fragments being eluted from a gel 2a in the gel capillaries 2 of the gel capillary cartridge 1. Distance between the upper plate 5 and the lower plate 6 can be changed. In order to protect the gel capillaries 2 from crash and to mechanically reinforce the gel capillary cartridge 1, however, the upper plate 5 and lower plate 6 are tied together at their sides with a plastic ribbon (not shown) of a predetermined length. The plastic ribbon is a sheet-like ribbon of around 0.5 mm thick, around 2 cm wide, and 20 to 30 cm length. The gel capillaries 2 are made of silica covered with polyimid resin on its surface. The gel capillaries 2 can be bent as they are thin in the diameter and has the polyimid covered on the surface. The gel capillaries 2 are bonded to the upper plate 5 and lower plate 6 as shown in FIG. 3a or are fixed with rubber rings 14 for holding capillary tubes as shown in FIG. 2a, with the upper plate 5 and sample injection plate 3 mechanically aligned with faucet joint and screwed together. Similarly, the lower plate 6 and a detector portion 7 are connected together.

The electrophoresis gel migration apparatus can be made small as numbers of the gel capillaries 2 can be bundled together and bent so that they can be contained in a narrow space for their long gel capillary migration paths. For the accommodation, it is effective that the numbers of the gel capillaries 2 should be gathered in a way that the gel capillaries 2 are sandwiched between two sheets of polymer film. In the way, if the gel capillary migration path used is 50 cm long, for example, an electrophoresis plate needed is around 60 cm long for slab gel. The gel capillaries 2 then can be bent to a length shorter than 20 cm for accommodation.

The upper plate 5, as described above, is tightly coupled with the sample injection plate 3 having sample wells 4 of 0.3 mm diameter, four in a column thereof and 25 in a row thereof at a pitch of 5 mm. It is designed that each of the gel capillaries 2 and their respective sample wells 4 should be aligned. The upper plate 5, as described above, has upper ends of the gel capillaries 2 arranged roughly at thereon in the two dimensions of columns and rows at the 5 mm pitch, while the lower plate 6 has the lower ends aligned closer than the above on a straight line at a pitch of 1 mm. The lower plate 6 is attached to and coupled with detector portion 7. The gel capillary cartridge 1 can be attached with or detached from the sample injection plate 3 and detector portion 7. Couplings of the gel capillaries 2 with the lower plate 6 are protected by rubber rings 14 for holding capillary tubes as shown in FIG. 2a. Similarly, couplings of the gel capillaries 2 with the sample injection plate 3 are protected by the rubber rings 14 for holding capillary tubes. The rubber rings 14 for holding capillary tubes are ignored and not shown in FIGS. 1b, 2b, 2c, 3a, 3b, and 5. The rubber rings 14 for holding capillary tubes can be made of teflon or rubber as well. A DNA sample that has been separated by the gel capillaries 2 that is an electrophoresis separator of the sample, is eluted from gel 2a in the gel capillaries 2 and enters the detector portion 7. FIG. 1b is a cross section A of FIG. 1a in the vicinity of the sample injection plate 3. As any of the gel capillaries 2 is coupled with the upper plate 5, the sample injected into the corresponding one of the sample wells 4 contacts the gel 2a. The gel capillaries 2 thus can be immersed in the upper buffer solution 18 as shown in FIG. 3a.

The embodiment 1 uses a sample adjusting titer plate having holes of 3 mm diameter aligned at the same intervals of as the sample injection plate 3 in addition to the sample injection plate 3 to inject the gel 2a into the sample. The titer plate has thin silicon rubber film lined on a bottom thereof. The titer plate is laid on the sample injection plate 3. The silicon rubber film can be broken with a needle or the like to make holes of around 0.5 mm diameter. In this way, the sample in the holes of the titer plate can be easily injected into the gel 2a.

The upper plate 5 of the gel capillary cartridge 1 in the embodiment described so far has the upper ends of the gel capillaries 2 arranged in the two dimensions, but may have them in on dimensions, or in a straight line.

Figure 2B:
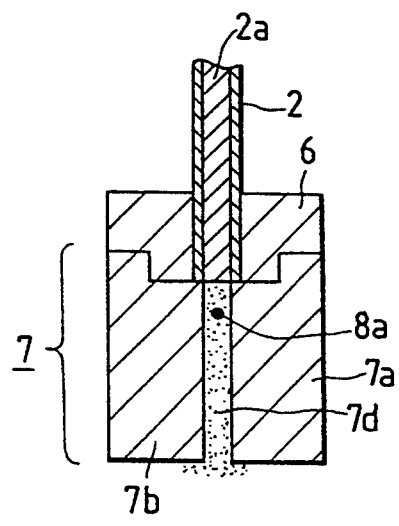
Figure 2C:
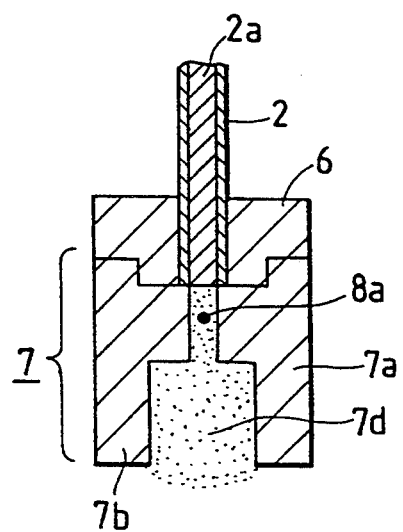

The detector portion 7 is coupled with the lower plate 6 of the gel capillary cartridge 1 as shown in FIGS. 2a, 2b, or 2c which is a cross section B of FIG. 1a. The migrated DNA sample elutes from the gel 2a before migrating in a lower buffer solution 7d or a hollow portion filled with the gel. An excitation light 8a is irradiated to excite a fluorescence label of the DNA sample in a direction parallel with the line of the lower ends of the gel capillaries 2. The hollow portion that is an irradiation light path for the excitation light 8a is formed of bulkheads 7a and 7b of two silica plates. In the detector portion 7, as shown in FIGS. 2a and 2b, the excitation light source 8 for exciting the fluorescence label irradiates at a position around 0.5 mm in front of the lower ends of the gel capillaries 2 in a gap of 0.1 mm formed by the bulkheads 7a and 7b of the two silica plates placed in parallel. FIG. 2c is a variation of the example in FIG. 2b that the lower buffer solution 7d or the gel can be easily immersed and contact the lower ends of the gel capillaries 2 from which the migrated DNA sample. The gap mentioned above is filled with the lower buffer solution 7d or the gel and serves as the path for the excitation light 8a. The excitation light 8a of the excitation light source 8, for example, a laser beam, reflected by a reflection mirror 9 can irradiate at the position around 0.5 mm above the lower ends of the gel capillaries 2 so that it can irradiate the DNA sample eluting from all the gel capillaries 2 at substantially the same time. So that in FIGS. 2b and 2c, the excitation light 8a is irradiated in a direction perpendicular to the drawing.

A number of the gel capillaries 2 used in the embodiment 1 is 100. Fluorescent signals can be obtained from an range of around 10 cm on the basis of the elution of the DNA sample as the excitation light 8a is irradiated. The fluorescent signals are detected by a photodetector 11, such as a line sensor, through a lens system 10 and a filter (not shown) at substantially the same time. The detected fluorescent signals are processed by a data processor 12 before fed out to an output device 13, such as a display.

If directly irradiated to the gel capillaries 2, the excitation light 8a (the laser beam here) is diverged, so that it cannot irradiate the number of the gel capillaries 2 at the same time. To solve such a difficulty, there can be a method that portions of the gel capillaries 2 to be irradiated are immersed in the lower buffer solution 7d to make diffraction differences little so that scatter of the light at the tube interface of the gel capillaries 2 as the excitation light 8a is irradiated for the detection of the fluorescent signals. It, however, is not always sufficient. There could be a better method that the detector portion 7 has no capillary tubes provided therefor. In the embodiment 1, the DNA sample is eluted from the gel capillaries 2, and the excitation light 8a is irradiated in a state of no capillary tubes or a state similar to it before the fluorescent signals are detected.

Figure 3B:
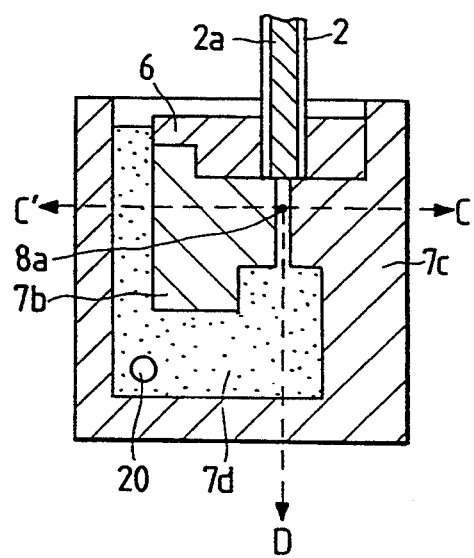
FIG. 3b is a cross-section of a variation of a portion around the fluorescence detector portion of the embodiment.

As shown in FIG. 3a, a detector is kept in a lower buffer vessel 7c, and a voltage is applied between an upper electrode 19 and a lower electrode 20 in the upper buffer vessel 17 filled with the upper buffer solution 18 before migration starts. The lower part of the electrophoresis gel migration apparatus shown in FIG. 3a can be modified as shown in FIG. 3b. In FIGS. 3a and 3b, the excitation light 8a for exciting the fluorescence label is irradiated in a direction perpendicular to the drawing so that the DNA sample eluting in the path for the excitation light 8a can generate fluorescent light. The fluorescent light is detected in a direction C or C' of a plane formed of transparent silica or a direction D. If the fluorescent light is detected in the direction C or C', for example, a fluorescent image of around 10 cm long is made small to one by four before detected by an image line sensor, for example, of 25 mm long of the S3902, the Hamamatsu Photonix Inc., a diode array equipped with an image amplifier, or a CCD detector. If the fluorescent image is detected in the direction C shown in FIG. 3b, it has the advantage that it has less effect due to reflection of the light by the surface than the one C in FIG. 3a.

Embodiment 2

Figure 5:
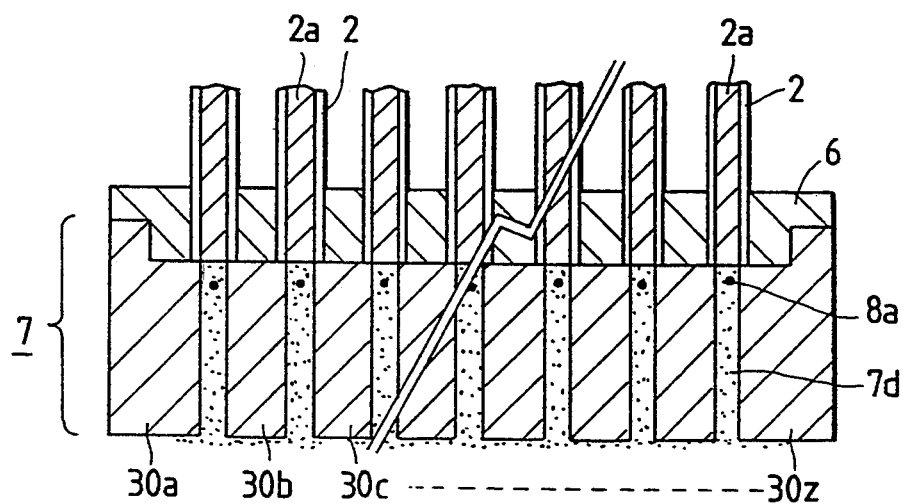

In turn, the following describes an embodiment 2 of the present invention by referring to FIG. 4. In the embodiment 2, lower ends of a gel capillaries 2 are arranged and fixed in two dimensions of columns and rows on a lower plate 6 of a gel capillary cartridge 1 so that numbers of the lower ends of the gel capillaries 2 can be collected in a narrow area. DNA sample eluting from the lower ends of the gel capillaries 2 are detected by a two-dimensional detector 7. In the figure, the lower ends of the gel capillaries 2 are arranged and fixed at a pitch of 1 mm in the columns and rows on the lower plate 6. The detector portion 7 has a group of detectors any of which is constructed as shown in FIG. 2a or 2b. That is, as shown in FIG. 5, an excitation light 8a irradiates at a position around 0.5 mm below the ends of the gel capillaries 2 in a space filled with a lower buffer solution 7d or gel in a direction perpendicular to the drawing. In the embodiment 2, bulkheads 30a through 30z for forming the space of around 0.1 mm gap as paths for the excitation light 8a may be non-transparent as lights generated from the DNA sample can be detected below the detector portion 7. The detector portion 7 is provided in the lower buffer solution 7d or the gel in a lower buffer solution 7d. The excitation light 8a is reflected by a reflection mirror 9 to irradiate below the all the lower ends of the gel capillaries 2 in the lower buffer vessel 7c (not shown in FIG. 4) at substantially the same time by means of prisms 16a and 16b provided one on each sides of the detector portion 7. Fluorescent signals from DNA samples eluted from the gel capillaries 2 are all detected at substantially the same time by the two-dimensional detector portion 7 through an image reflection mirror 15, a lens system 10, and a filter (not shown). A bottom plate of the lower buffer vessel 7c (not shown in FIG. 4) is made of silica plate. Of course, for example, the reflection mirror 9 can be moved to sequentially scan the line excitation light 8a over the space around the area from one side of the detector portion 7 to a point at which the lower buffer solution 7d or the gel is filled with and the DNA sample elutes. Alternatively, the reflection mirror 9 can be made to irradiate at the same time the whole line of the space around the area from the one side of the detector portion 7 to the point at which the lower buffer solution 7d or the gel is filled with and the DNA sample elutes. The prisms 16a and 16b can be provided either on an inside or the outside of the lower buffer vessel 7c (not shown in FIGS. 4 and 5).

Note that parts of the electrophoresis gel migration apparatus above the gel capillaries 2 are not shown in FIG. 4.

In the embodiments described so far, the upper plate 5 of the gel capillary cartridge 1 and the sample injection plate 3 can be attached or detached together. The lower plate 6 of the gel capillary cartridge 1 and the detector portion 7 also can be attached or detached together. Alternatively, the upper plate 5 and the sample injection plate 3 can be integrated and the lower plate 6 and the detector portion 7 can be integrated, and the two integrated couples can be assembled together to make another form of gel capillary cartridge. More alternatively, only either of the two couples mentioned above can be integrated to make still another form of gel capillary cartridge. If the sample injection plate 3 and the detector portion 7 are integrated with the gel capillary cartridge 1, the gel capillary cartridge 1 can be attached with or detached from the upper buffer vessel 17 and the lower buffer vessel 7c at ends of the sample injection plate 3 and the detector portion 7, respectively.

In usual electrophoresis (one-dimensional electrophoresis), the sample is separated in one-dimensional way in a direction x. In the so-called two-dimensional electrophoresis, on the other hand, the separated sample has an enzyme poured thereon to make some action, is separated again in a direction (direction y) perpendicular to the direction x to develop in the two dimensions. The two-dimensional electrophoresis provides more detailed separation of the sample than the one-dimensional one. It may occur that even the two-dimensionally separated pattern on the slab gel is lack of amount of information. In this case, it is effective that the slab gel having the sample separated thereon should be divided into numbers of sections, the sample contained in each of the sections should be made to act with enzyme or a DNA probe or the like, and a product made through the action should be gel-separated again to obtain more information. For the third electrophoresis separation, the present invention can use a capillary array distributed in two dimensions. It can be regarded as a separation in a direction z in relation to the ones in the directions x and y. The final information, or the third dimension information, can be obtained in terms of a time-varying signal from measuring point distributed in the two dimensions. Alternatively, it can be obtained in a way that the capillaries should be rearranged in a line, the signals should be obtained, and then data should be stored as if they were obtained in the two-dimensional arrangement.

It is not practical to employ a usual three-dimensional electrophoresis having flat or block gel used therein, as the gel cross sections are too wide, allowing overcurrent to flow. In the gel capillary electrophoresis, current flowing through each of the gel capillaries is so small that no problems can be due to heat generation.

For the purpose of illustration only, the parts of the apparatus shown in FIGS. 1 to 5 are drawn different from those of the actual apparatus in proportions of shapes. The features of the present invention are as follows. The electrophoresis gel migration apparatus according to the present invention can increase throughput to a great extent as it can have numbers of gel capillary migration paths incorporated in the narrow detection end area without affecting sample injection. Also, it can reduce sample injection work to a great extent as the arrangement of the sample wells on the sample injection plate are matched with that of the sample holes on the titer plate. Further, the apparatus can be made small as the gel capillaries can be bent so that the long gel capillary migration paths can be incorporated in the narrow space. If the gel capillary migration paths used are 50 cm long, for example, the slab gel requires a migration plate of around 60 cm long, resulting in a large scale apparatus, while the gel capillaries can be bent to within 20 cm to contain. In order to have the migration paths as much as 100, the slab gel requires the migration plate of 40 cm wide or more, while the two-dimensional gel capillary arrangement allows the detector area to be made as narrow as $1 \times 1$ cm or less.

What is claimed is:

1. An electrophoresis gel migration apparatus comprising gel capillaries being filled with gel, an excitation light source, fluorescent light detecting means, and means applying an electric field to the gel; characterized in that the gel capillaries are arranged to provide a density of sample introduction ends of the gel capillaries that is less than that of fluorescence detecting ends of the gel capillaries.

2. An electrophoresis gel migration apparatus according to claim 1, characterized in that sample introduction ends of the gel capillaries are arranged in two dimensions.

3. An electrophoresis gel migration apparatus according to claim 1, characterized in that the fluorescence detecting ends of the gel capillaries are arranged in one dimension.

4. An electrophoresis gel migration apparatus according to claim 1, characterized in that the sample having migrated through the gel capillaries elutes into a gap filled with buffer solution or the gel before being detected.

5. An electrophoresis gel migration apparatus according to claim 4, characterized in that the sample introduction ends are arranged side-by-side in laterally spaced rows and the fluorescent detecting ends of the gel capillaries are arranged linearly in a row one after the other, said excitation light source being arranged to irradiate all of the migrating samples at positions at which the samples elude from the capillaries into said gap filled with buffer solution or the gel substantially simultaneously.

* * * * *